US010820816B2

(12) United States Patent
Jackson et al.

(10) Patent No.: US 10,820,816 B2
(45) Date of Patent: Nov. 3, 2020

(54) SYSTEM FOR A BRAIN-COMPUTER INTERFACE

(71) Applicants: UNIVERSITY OF LEICESTER, Leicestershire (GB); UNIVERSITY OF NEWCASTLE UPON TYNE, Newcastle upon Tyne (GB); IP2IPO INNOVATIONS LIMITED, London (GB)

(72) Inventors: Andrew Jackson, Newcastle upon Tyne (GB); Tim Constandinou, London (GB); Amir Eftekhar, London (GB); Rodrigo Quian Quiroga, Leicestershire (GB); Joaquin Navajas Ahumada, Leicestershire (GB)

(73) Assignees: UNIVERSITY OF LEICESTER, Leicester (GB); UNIVERSITY OF NEWCASTLE UPON TYNE, Newcastle upon Tyne (GB); IP2IPO INNOVATIONS LIMITED, London (GB)

( * ) Notice: Subject to any disclaimer, the term of this patent is extended or adjusted under 35 U.S.C. 154(b) by 333 days.

(21) Appl. No.: 15/115,616

(22) PCT Filed: Jan. 29, 2015

(86) PCT No.: PCT/GB2015/050217
§ 371 (c)(1),
(2) Date: Jul. 29, 2016

(87) PCT Pub. No.: WO2015/114347
PCT Pub. Date: Aug. 6, 2015

(65) Prior Publication Data
US 2017/0164852 A1  Jun. 15, 2017

(30) Foreign Application Priority Data
Jan. 30, 2014 (GB) .................................. 1401613.3

(51) Int. Cl.
*A61B 5/04* (2006.01)
*A61B 5/00* (2006.01)
*G06F 3/01* (2006.01)

(52) U.S. Cl.
CPC .............. *A61B 5/04* (2013.01); *A61B 5/4064* (2013.01); *G06F 3/015* (2013.01)

(58) Field of Classification Search
None
See application file for complete search history.

(56) References Cited

U.S. PATENT DOCUMENTS

2003/0073917 A1* 4/2003 Echauz ................ A61B 5/0476
600/510
2005/0090756 A1* 4/2005 Wolf ........................ A61N 1/08
600/546

(Continued)

OTHER PUBLICATIONS

Rizk et al. A fully implantable 96-channel neural data acquisition system. Journal of Neural Engineering, Institute of Physics Publishing, Bristol, GB, vol. 6, No. 2, Apr. 1, 2009.*

(Continued)

*Primary Examiner* — Etsub D Berhanu
(74) *Attorney, Agent, or Firm* — Marshall, Gerstein & Borun LLP

(57) ABSTRACT

The invention provides a two-step approach to providing a BCI system. In a first step the invention provides a low-power implantable platform for amplifying and filtering the extracellular recording, performing analogue to digital conversion (ADC) and detecting action potentials in real-time, which is connected to a remote device capable of performing the processor-intensive tasks of feature extraction and spike classification, thus generating a plurality of predetermined templates for each neuron to be used in a second processing step. In the second step the low-power implantable platform amplifies and filters the extracellular recording, performs (Continued)

ADC and detects action potentials, which can be matched on-chip to the predetermined templates generated by the external receiver in the first step. This two-step approach exploits the advantages of both offline and online processing, providing an effective and safe method for performing multiple recordings of single-neuron activity, for research or monitoring applications or for control of a remote device.

17 Claims, 10 Drawing Sheets

(56) References Cited

U.S. PATENT DOCUMENTS

| | | | |
|---|---|---|---|
| 2006/0167369 A1* | 7/2006 | Montgomery, Jr. | A61B 5/04001 600/544 |
| 2009/0082637 A1* | 3/2009 | Galperin | G06F 19/321 600/300 |
| 2009/0082692 A1* | 3/2009 | Hale | A61B 5/0476 600/544 |
| 2009/0124919 A1* | 5/2009 | Ginosar | G06K 9/00543 600/544 |
| 2009/0220425 A1* | 9/2009 | Moxon | A61B 5/0484 424/9.2 |
| 2012/0203129 A1* | 8/2012 | Rennaker, II | A61B 5/0002 600/544 |
| 2013/0261471 A1* | 10/2013 | Saha | A61B 5/4052 600/484 |

OTHER PUBLICATIONS

Quiroga et al. Unsupervised Spike Detection and Sorting with Wavelets and Superparamagnetic Clustering. Neural Comput. Aug. 2004; 16(8):1661-1687.*
Jochum et al. Integrated circuit amplifiers for multi-electrode intracortical recording. Journal of Neural Engineering, 6 (2009). (Year: 2009).*
Lewicki. A review of methods for spike sorting: the detection and classification of neural action potentials. Comput. Neural Syst. 9 (1998) R53-R78. (Year: 1998).*
International Search Report and a Written Opinion for International Application No. PCT/GB2015/050217, dated Apr. 17, 2015.
Chinese Patent Application No. 201580006550.7, Notification of the First Office Action, dated Jun. 29, 2018.
European Patent Application No. 15702568.5, Examination Report, dated Jan. 9, 2018.
European Patent Application No. 15702568.5, Examination Report, dated Sep. 25, 2018.
Harrison et al., A low-power low-noise CMOS amplifier for neural recording applications, IEEE Journal of Solid-State Circuits, 38(6):958-65 (Jun. 2003).
Harrison, The design of integrated circuits to observe brain activity, Proceedings of the IEEE, pp. 1203-1216 (Jul. 1, 2008).
Japanese Patent Application No. 2016-549484, Notification of Reason(s) for Rejection, dated Oct. 9, 2018.
PHAM, A real-time neural signal processing system for dragonflies, Master of Science Thesis, The University of Arizona, Department of Electrical and Computer Engineering, retrieved from the Internet at: <http://www.thehigginslab.webhost.uits.arizona.edu/pubs/2011_thuy_pham_thesis.pdf> (Jan. 1, 2011).

* cited by examiner

· · · · · · · · · · Class 1
———— Class 2
— — — Class 3

SYSTEM FOR A BRAIN-COMPUTER INTERFACE

CROSS-REFERENCE TO RELATED APPLICATIONS

The present application is the US national phase of International Patent Application No. PCT/GB2015/050217, filed Jan. 29, 2015, which claims priority to United Kingdom Application No. 1401613.3, filed Jan. 30, 2014. The priority application, GB 1401613.3, is hereby incorporated by reference.

BACKGROUND

Neuroscientists can record extracellular action potentials, or spikes, generated by neurons in order to understand how information is represented and transmitted through the nervous system.

Until recently, these experiments typically involved sampling small numbers of neurons (e.g. fewer than 15) over short sessions of a few hours, but with advances in chronic electrode arrays it has become possible to record spikes from large numbers of neurons (e.g. more than 15) over several months. These techniques inspired the development of brain-computer interfaces (BCIs) that communicate directly with the nervous system, for therapeutic benefit or research studying brain processes. A BCI can enable communication between the brain of an animal or patient and any external computer, data processing system or any connected electronic device. One example of such is a brain-machine interface (BMI) using neural signals from the cortex of a paralysed patient to operate assistive devices such as a robotic prosthesis.

To obtain accurate results, a brain-computer interface, or any other system for recording single-neuron activity, should detect action potentials by means of extracellular recordings and identify which action potentials correspond to which neuron. Action potentials are classified according to their shape, based on the principle that each neuron produces action potentials with a stereotyped waveform. Data is relayed to an external computer where information or commands are processed based on the activity of several individual neurons.

BCI's have been proposed which have spike sorting modules for implantation into the brain to sort the action potentials according to the shapes of the stereotyped waveforms, but these involve complex computations that are difficult to implement on-chip and therefore, when processing data from many recording electrodes, they dissipate excessive power which may cause overheating, and also place restrictions on the extent to which the implantable device can be miniaturised. This is therefore extremely dangerous to the health of the subject of the neural monitoring. To address this problem, designers have sought to remove as much processing from the implantable module as possible, limiting the implantable module to sensing technology and performing all signal processing at an external device.

While this simplifies the implantable device, it places a large load on the communication overheads between the implantable device and the external processing circuitry. The monitored signal must be transmitted in its entirety to the external processing circuitry, and this consumes a large amount of bandwidth, much of which is wasted through transmission of redundant information such as background noise and periods of a signal which do not contain action potentials. In turn, this slows down the spike detection and sorting process, which may potentially be critical in therapeutic applications.

SUMMARY

Embodiments of the present invention adopt a hybrid approach in which some of the processing functionality is performed at an external device, but some is performed locally in the implantable device. This reduces communication overheads, since the spike detection process and the template matching process are performed locally at the implantable device, and only the result of a comparison, or an action potential profile which has not previously been detected, need to be transmitted to external devices. The speed of the invention is therefore increased relative to conventional systems, without complicating the implantable device.

According to an aspect of the present invention there is provided a system for a brain-computer interface.

According to an aspect of the present invention there is provided an implanted device.

According to an aspect of the present invention there is provided a remote device.

Optional features are set out in the dependent claims.

Embodiments of the present invention provide a two-step approach to providing a wireless BCI system. In a first step a low-power implantable platform amplifies and filters an extracellular recording, performs analogue to digital conversion (ADC) and detects action potentials in real-time. The processor is wirelessly connected to an external receiver capable of performing the processor-intensive tasks of feature extraction and spike classification, thus generating a plurality of predetermined templates for each neuron to be used in a second processing step. In the second step the low-power implantable platform amplifies and filters the extracellular recording, performs ADC and detects action potentials, which can be matched on-chip to the predetermined templates generated by the external receiver in the first step. This two-step approach exploits the advantages of both offline and online processing, providing an effective and safer method for performing multiple wireless recordings of single-neuron activity. Embodiments may be used for performing multiple single-cell recordings, for research or monitoring applications or for control of any external electronic device.

BRIEF DESCRIPTION OF THE DRAWINGS

The present invention will be described, by way of example only, with reference to the following drawings:

FIG. 10b is a wavetrace of the clusters of action potentials shown in FIG. 9a;

FIG. 10c is a wavetrace of the plurality of spike templates generated from the clusters of action potentials shown in FIG. 9a;

FIG. 11 is a chart showing the performance and relative processor time required for a variety of distance metrics;

FIG. 12 is a chart showing the effect of peak-alignment error on template matching performance.

DETAILED DESCRIPTION

Figure 1:
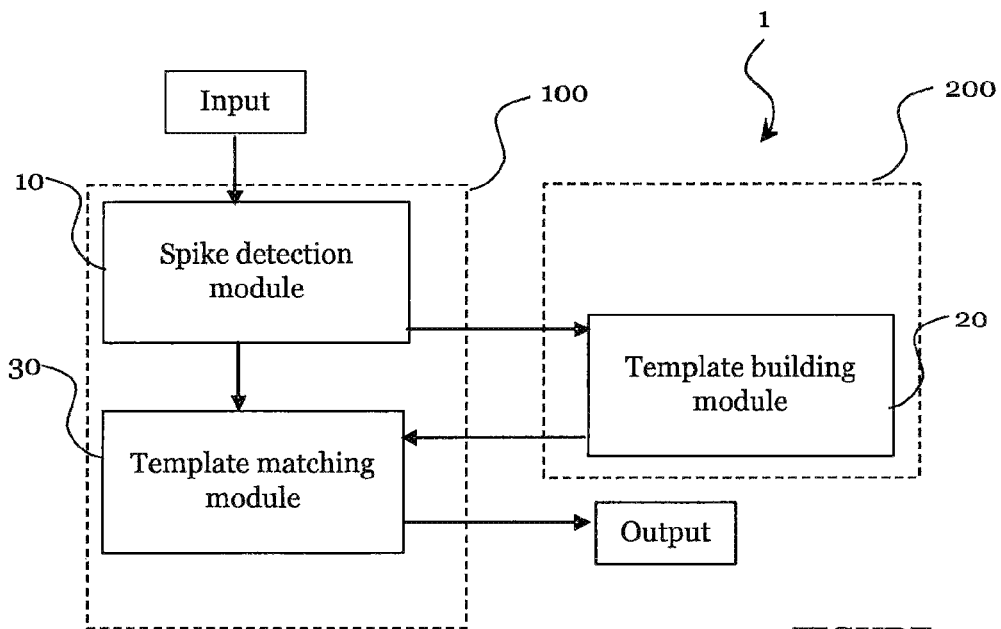
FIG. 1 is a schematic diagram of the wireless brain-machine interface of an embodiment of the present invention.

FIG. 1 shows a system 1 for a wireless brain-computer interface (BCI) according to an embodiment of the present invention. The BCI comprises a spike detection module 10, a template building module 20 and a template matching module 30. The template building module 20 communicates wirelessly with the spike detection module 10 and the template matching module 30. The spike detection module 10 can communicate with the template matching module 30. The spike detection module 10 and the template matching module 30 communicate directly through a wired connection and may be implemented on a single chip.

The spike detection module 10 and the template matching module 30 are arranged in a device 100 which is implanted in or near the brain, which is coupled to one or more electrodes for recording a signal at or near at least one neuron in the brain. The template building module 20 is arranged in a remote device 200 having a wireless connection with the implanted device 100. The remote device 200 could be intended for external use, with respect to the patient, or implanted at a separate site from the brain. The template building module 20 communicates wirelessly with the spike detection module 10 and the template matching module 30 through the wireless connection. The template matching module 30 may wirelessly transmit a result of a template matching process.

Alternatively, the system may be implemented through cable communication between the template building module 20 and the spike detection 10 and template matching modules 30. This embodiment does not offer the advantages of wireless communication but still offers an effective method for online and on-chip spike detection and sorting. Power consumption for the implanted device 100 can still be reduced through a reduction of the data rate through a cable connection. In a wired embodiment the remote device 200 may be implanted in another part of the body. The remote device 200 may be powered off unless required, in order to further reduce power consumption.

The embodiment therefore provides a two-part system including a low-power implantable platform 100 for detecting spikes and matching them with templates, wirelessly connected with an external receiver 200, which can perform the processor-intensive template building.

The spike detection module 10 detects action potentials generated by neurons in the brain, which are recorded using the one or more electrodes or a micro-contact voltage sensing technique, as is known in the art. Each of the one or more electrodes records a single site, or may record multiple sites. For each recording site, the spike detection module 10 may detect a plurality of action potentials generated by a plurality of neurons in close proximity to the recording site.

The shape of a spike is the shape formed by the wavetrace of a detected action potential. The template building module 20 generates a spike template which corresponds to a stereotypical shape for the action potential generated by a particular neuron. The template building module 20 generates the spike template for each stereotypical spike shape based on one or more of the action potentials detected by the spike detection module 10 so that future action potentials which have the same or similar shape can be identified on the basis of matching the detected action potential with the generated spike template. The template building module 20 may generate the spike template based on an average of a plurality of detected action potentials generated by a single neuron. The template building module 20 may generate a plurality of distinct spike templates based on a plurality of distinct action potentials generated by a plurality of distinct neurons. The template building module 20 stores the generated spike templates and provides the templates to the template matching module 30 when required.

The template matching module 30 is arranged to cluster action potentials generated by different neurons according to their shape. The template matching module 30 compares the action potential detected by the spike detection module 10 with the one or more spike templates generated by the template building module 20. The template matching module 30 outputs a signal according to a result of the comparison. The output signal may indicate a positive match between the action potential and one of the spike templates. The template matching module 30 may compare one or more detected action potentials to a plurality of predetermined spike templates generated by the template building module 20. The output signal may indicate one or more positive matches between the one or more action potentials and the plurality of predetermined spike templates. The template matching module 30 may wirelessly transmit the output signal to an external device.

In some instances, in the event of a negative comparison result, the template matching module 30 may transmit the detected action potential to the template building module 20 to generate a new template for the unknown spike shape, which may represent significant neural activity which has not previously been detected by the apparatus. However, a negative comparison may also be due to the fact that a detected signal is not an action potential at all, and in such cases, it is undesirable for the template building module 20 to be activated, since any template generated in these circumstances would be unwanted. The template building module 20 may determine whether to generate the new template or not, based on the similarity between a plurality of unknown spike shapes. The template building module 20 is able to distinguish between an unknown action potential and a noise signal which is not an action potential, since a plurality of noise signals will not generally have a similar shape to each other.

The template matching module 30 may have local storage for buffering generated templates received from the template building module 20. The size of the storage may be selected in accordance with the user's requirements. If the expected neural activity represents a relatively small number of distinct action potential types, local storage of templates at the template matching module 30 is an effective way to improve the efficiency of the invention as the implantable platform can effectively operate unsupervised. In more complex cases, the local storage capacity of the template matching module may not be sufficient to store all of the required templates, and in such cases, regular communication with the template building module 20 is more efficient.

In both cases, periodic updating of the templates may be required to compensate for changes in the recording conditions, which may have a global effect on the action potentials, such as changes in the background noise, or shifts in the action potential shape. The template building module 20 may perform periodic updating of the templates by averaging the shape of the latest detected action potentials which correspond to the template.

The ability to allow the implantable device 100 to operate unsupervised is dependent in part on the optimised nature of the spike sorting and template matching processes, which is explained in detail below. This in turn enables the division of the functionality of the invention between the implantable device 100 and the external template building module 20. In addition, scalability in terms of the number of channels that can be recorded is provided through avoidance of large power and/or bandwidth demands.

Figure 2:
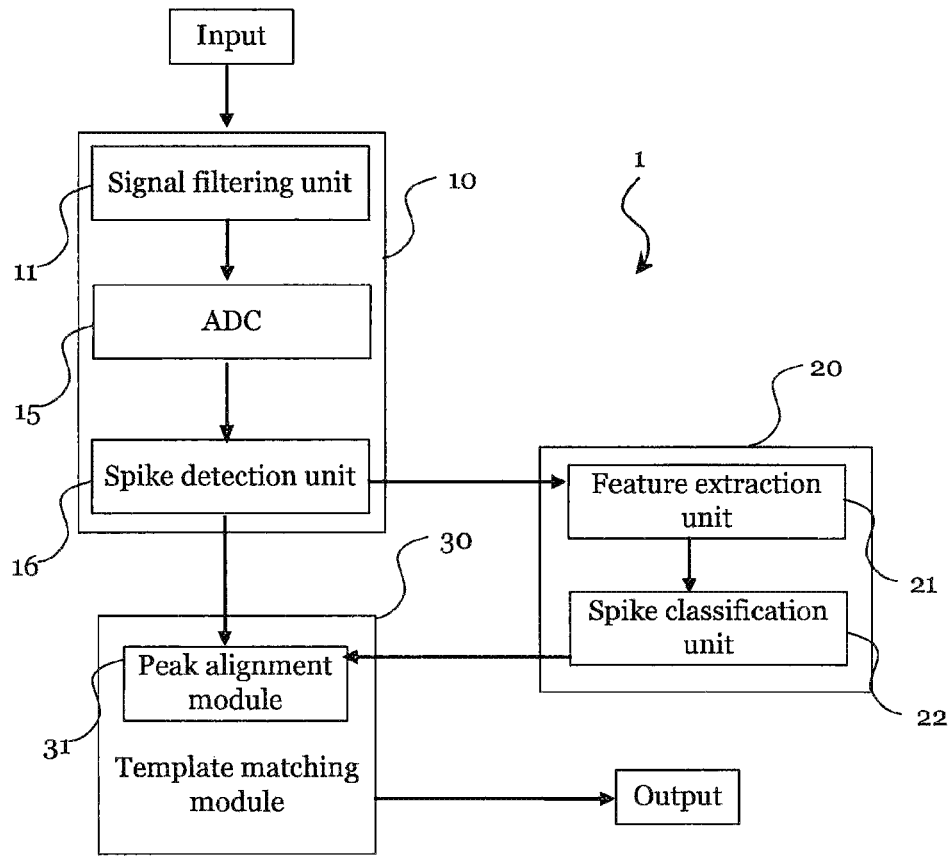
FIG. 2 is an expanded schematic diagram of the wireless brain-machine interface of an embodiment of the present invention.

FIG. 2 shows that the spike detection module 10 comprises a signal filtering unit 11, an analogue-digital converter (ADC) 15 and a spike detection unit 16. The signal filtering unit 11 is configured to filter a signal recorded at or near at least one neuron in the brain using a bandpass filter 13. The extracellular recording may include one or more action potentials generated by a plurality of neurons in close proximity. The signal filtering unit 11 applies a filter 13 configured to increase the signal-to-noise ratio (SNR) of the extracellular recording.

In an embodiment, the signal filtering unit 11 applies one of an elliptic filter, a Butterworth filter and a Bessel filter. Alternatively, the signal filtering unit 11 may apply any other filtering implementation.

The signal filtering unit 11 is configured to filter the extracellular recording in real-time. The filter 13 applied by the signal filtering unit 11 may be a causal filter which calculates each data point based on data points which precede the data point in question, but not those that follow after.

As shown in FIG. 2, the ADC 15 may be positioned before the spike detection unit 16, so that spike detection is performed in the digital domain. However, in another embodiment, it would also be possible for the ADC 15 to be positioned after the spike detection unit 16, so that spike detection is performed in the analogue domain.

Figure 3:
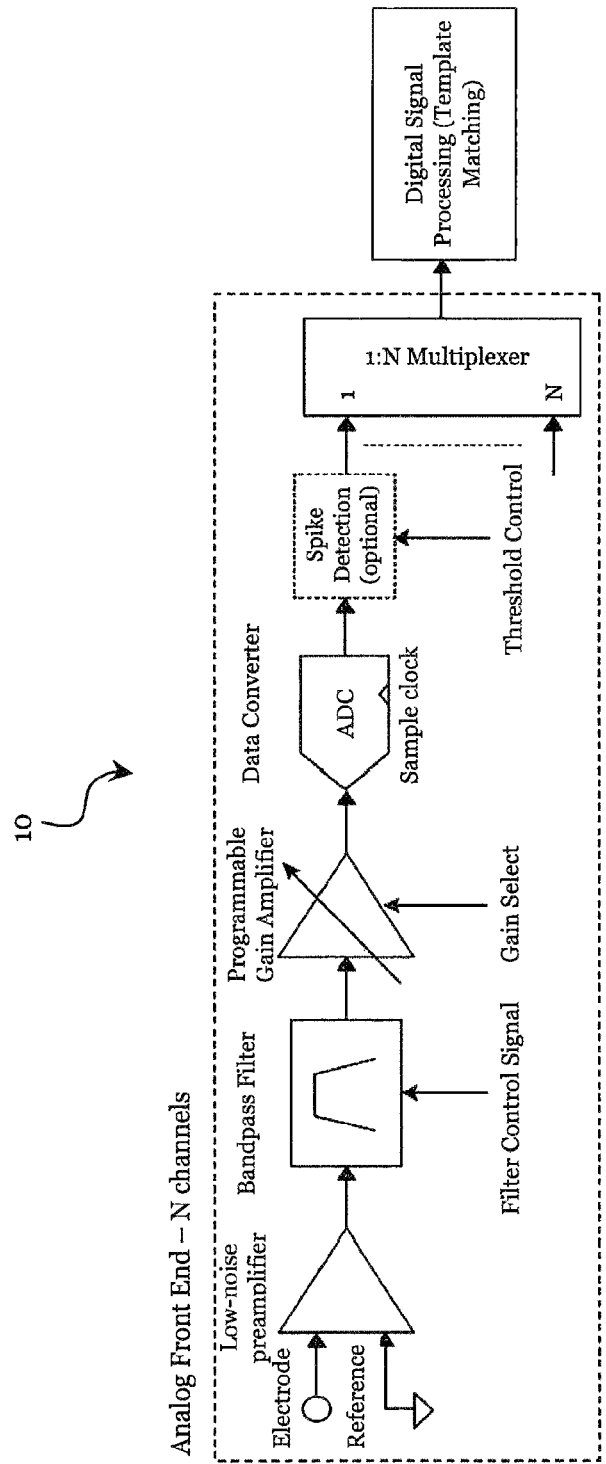
FIG. 3 is a schematic diagram of the spike detection module of FIG. 1.

FIG. 3 is a schematic diagram of the spike detection module 10 which shows the signal filtering unit 11 comprises a preamplifier 12, the filter 13, and an optional gain amplifier 14. The pre-amplifier 12 is configured to maximise the SNR of the extracellular recording before filtering is applied. In an embodiment, the preamplifier 12 is a low noise, low power preamplifier. The gain amplifier 14 may be a programmable gain amplifier, configured to maximise the input dynamic range to the ADC 15. The spike detection unit 16 may be optional, in case the detection is done directly by template matching in the filtered data.

In an embodiment, the spike detection module 10 may be implemented as an integrated circuit. The integrated circuit includes the signal filtering unit 11, ADC 15 and the spike detection unit 16 on-chip. Communication off-chip can be reduced from raw data to spike packets, considerably reducing the data rate for off-chip communication. The power consumption for off-chip data communication is a function of bus capacitance, supply voltage and data rate. By transmitting spike packets, the off-chip data rate is reduced significantly, providing a reduced system power consumption.

Figure 4:
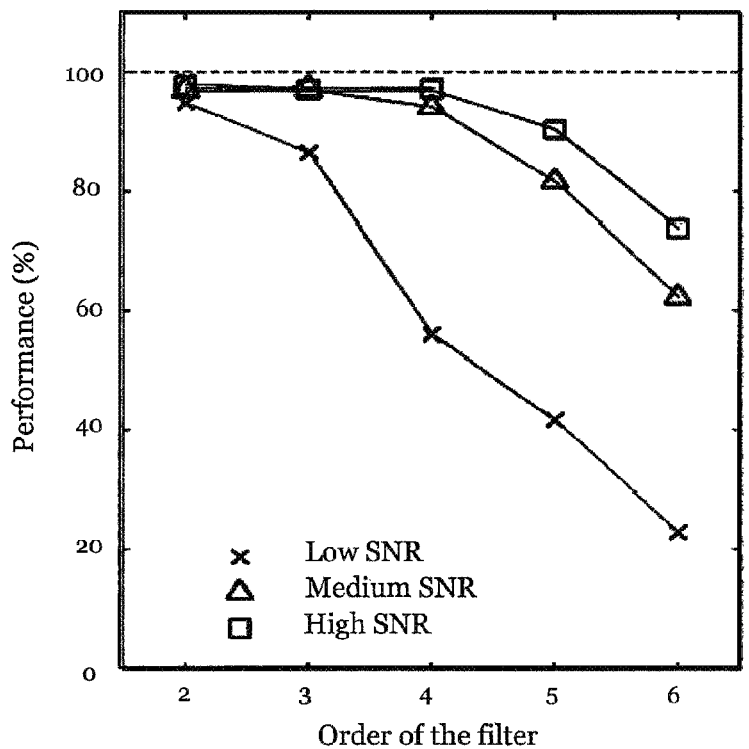
FIG. 4 is a chart showing the effect of filter order on spike detection performance.

FIG. 4 shows the effect of an order of the filter 13 on the performance of the spike detection unit 16, for signals having a high, medium and low SNR, with an elliptic filter. The filter 13 applied by the signal filtering unit 11 may be one of a $1^{st}$, $2^{nd}$, $3^{rd}$ or $4^{th}$ order filter. A lower order filter introduces a lower level of phase distortion.

Decreasing the passband width can increase the SNR of the extracellular recording. A passband which is too narrow can reduce the performance of the spike detection unit 16. In one embodiment, the performance of the spike detection unit 16 should be maintained at approximately 90% or higher, with respect to the percentage of accurately detected neural activity, as measured using techniques known in the art, based on processing of synthetic test signals.

Figure 5:
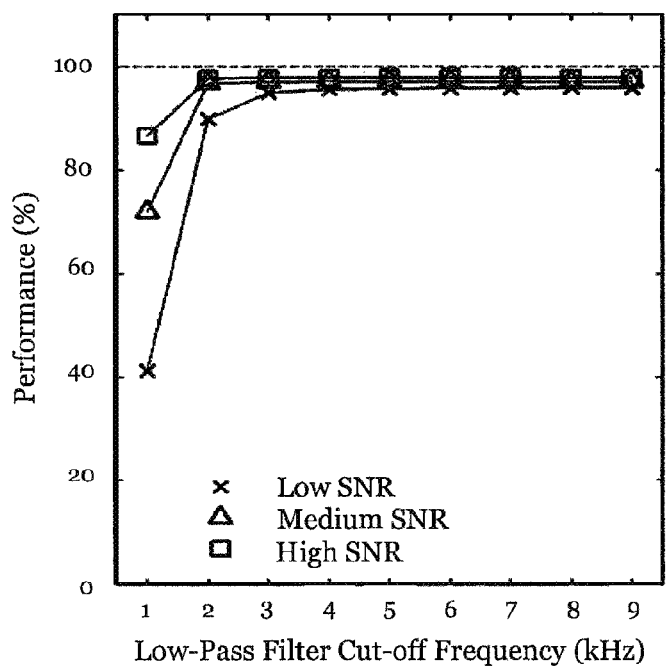
FIG. 5 is a chart showing the effect of low-pass cut-off frequency on spike detection performance.

FIG. 5 shows the effect of the low-pass cut-off frequency on the performance of the spike detection unit 16, for signals having a high, medium and low SNR. The low-pass cut-off frequency of the filter 13 is chosen such that the performance of the spike detection unit 16 is maximised. In an embodiment, the low-pass frequency is 3 kHz.

Figure 6:
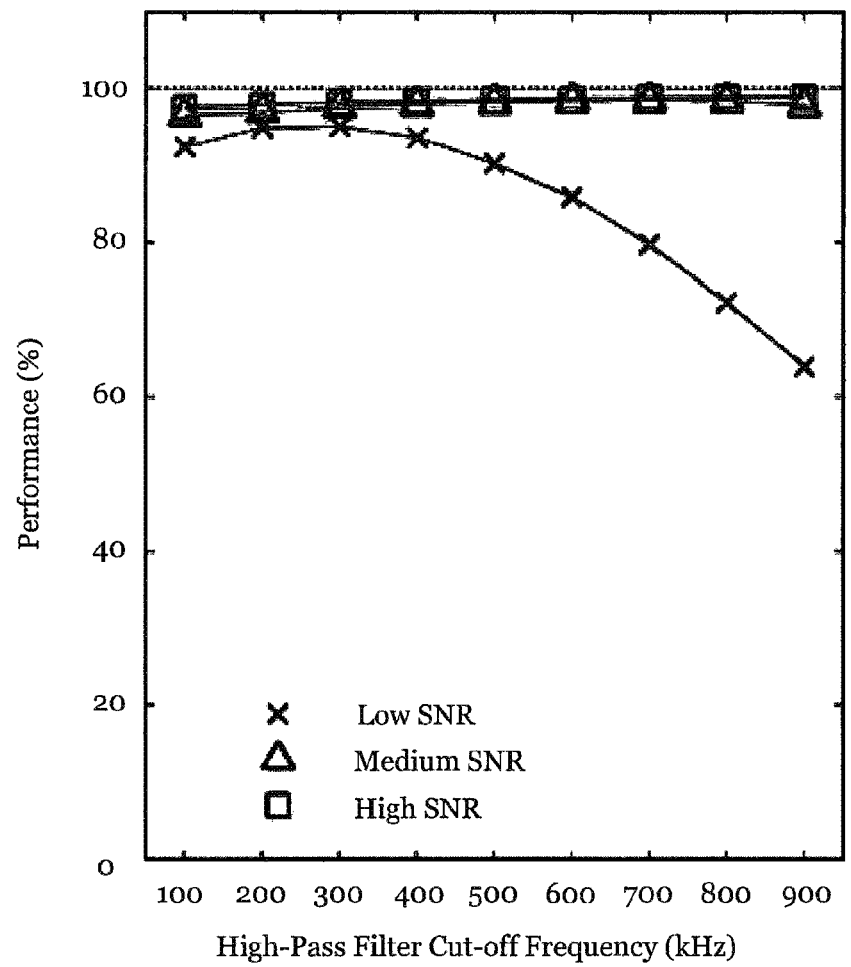
FIG. 6 is a chart showing the effect of high-pass cut-off frequency on spike detection performance.

FIG. 6 shows the effect of the high-pass cut-off frequency on the performance of the spike detection unit 16, for signals having a high, medium and low SNR. The high-pass cut-off frequency of the filter 13 is chosen such that the performance of the spike detection unit 16 is maximised. In embodiments of the present invention, the high-pass frequency is one of 100 Hz, 200 Hz or 300 Hz.

The ADC 15 is configured to convert the signal recorded near at least one neuron from an analogue signal into a digital signal. In an embodiment, the ADC 15 converts the filtered signal output by the signal filtering unit 11. Alternatively, the ADC 15 converts the extracellular recording to a digital signal, which is then filtered by the signal filtering unit 11. The filter 13 applied by the signal filtering unit in the digital domain may be a non-causal filter which calculates each data point based on data points which precede the data point in question as well as those that follow after.

A data rate of the extracellular recording may be altered by adjusting a sampling rate and resolution of the ADC 15. A reduced data rate of the extracellular recording provides a reduced level of power consumption in the spike detection module 10. A sampling rate or a resolution which is too low can reduce the performance of the spike detection unit 16 and the performance of the template building module 20. The performance of the spike detection unit 16 should be maintained at 80% or higher. If variation of the sampling rate and ADC resolution is the primary parameter in optimising the spike detection, in contrast to variation of the filtering, the power cost is such that the achievable performance may be less than if filtering were the primary parameter to be varied. Through control of each of filtering, sampling rate and ADC resolution, however, the performance of the spike detection unit 16 can be 90% or higher. The performance of the template building module 20 should be maintained at 50% or higher with respect to generation of templates from an artificially generated signal.

Figure 7A:
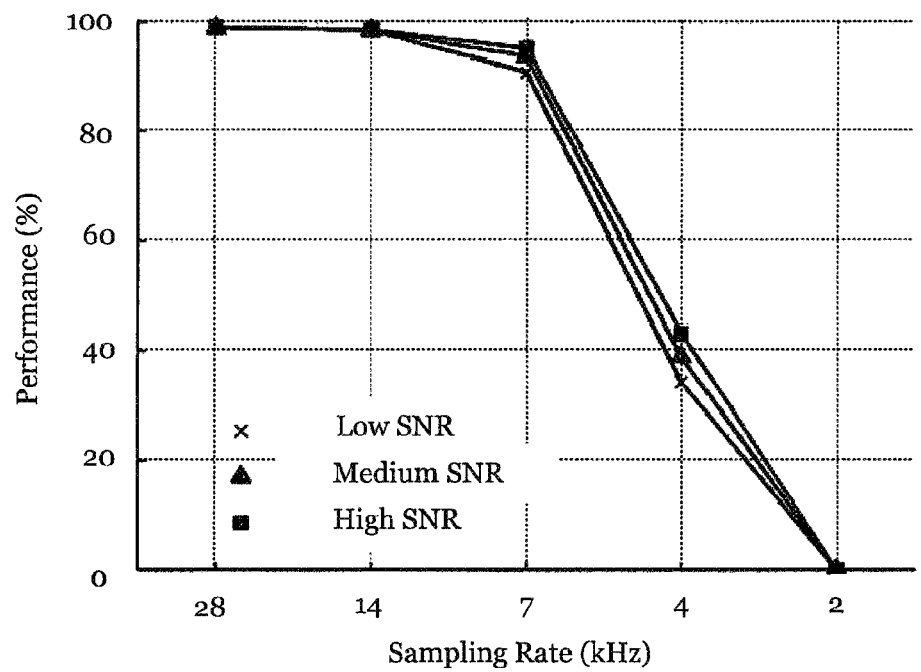
FIG. 7a is a chart showing the effect of ADC sampling rate on spike detection performance.
Figure 7B:
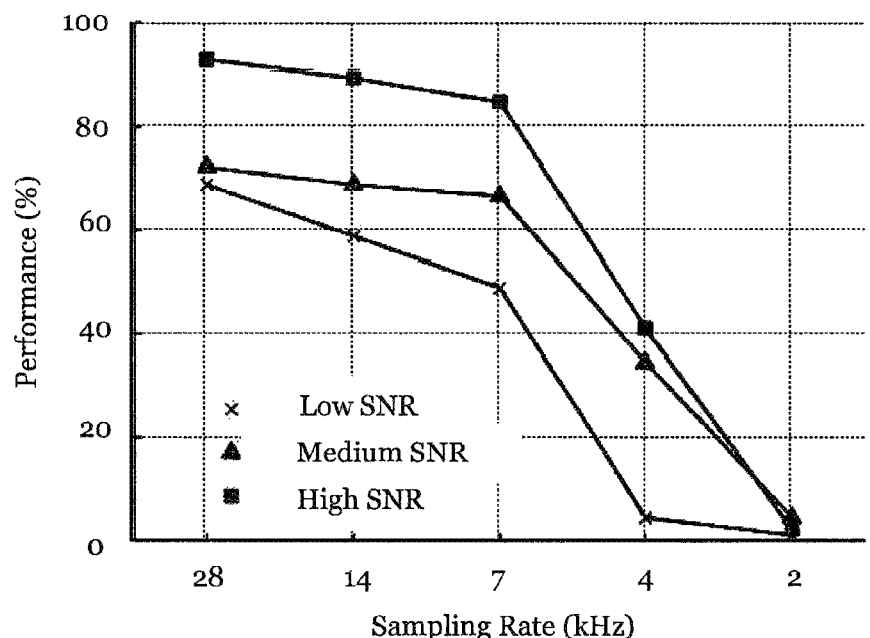
FIG. 7b is a chart showing the effect of ADC sampling rate on template building performance.

FIGS. 7a and 7b shows the effect of the ADC sampling rate on the performance of the spike detection unit 16 and template building module 20 respectively, for signals having a high, medium and low SNR. In an embodiment of the present invention, the sampling rate of the ADC 15 is larger than 7 kHz.

Figure 8A:
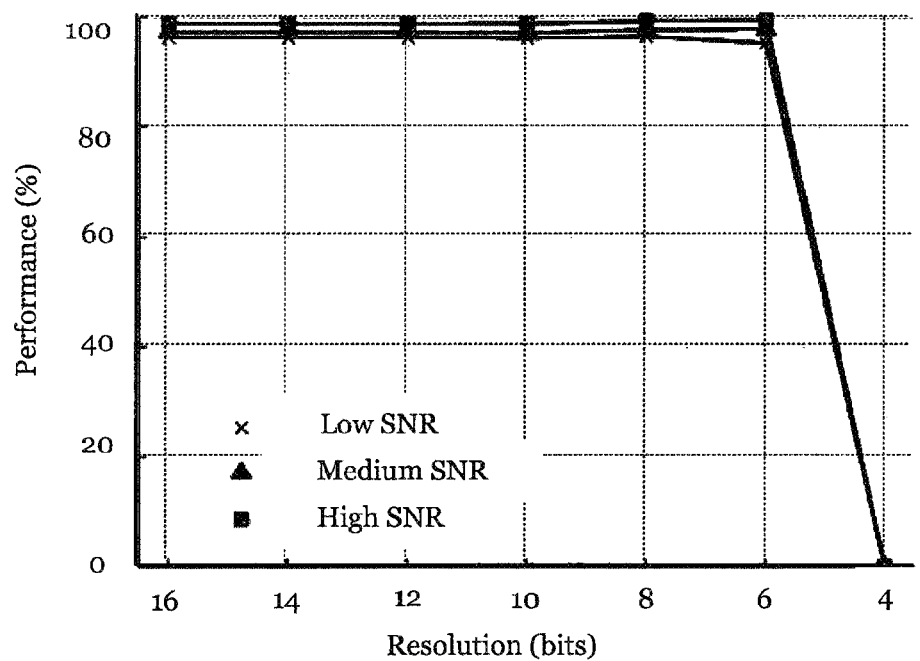
FIG. 8a is a chart showing the effect of ADC resolution on spike detection performance.
Figure 8B:
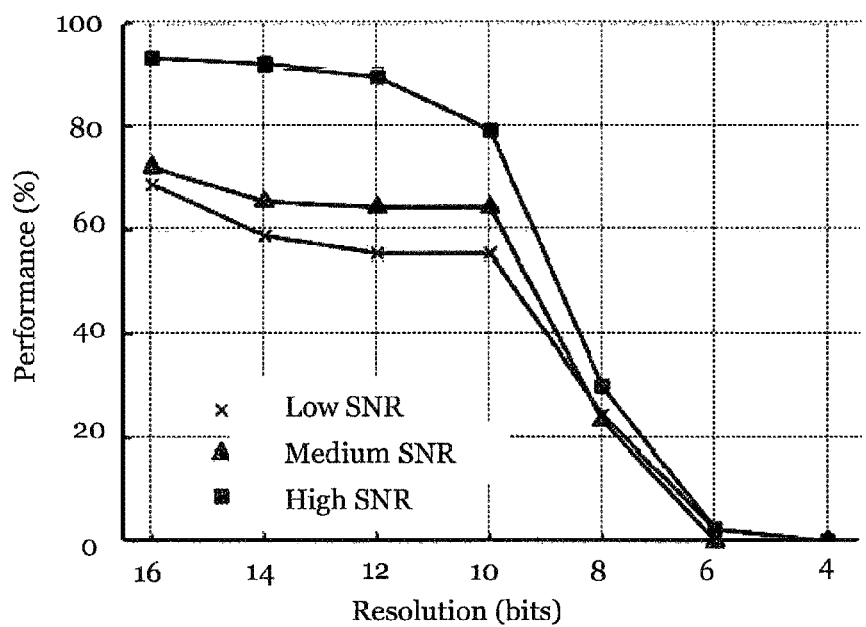
FIG. 8b is a chart showing the effect of ADC resolution on template building performance.

FIGS. 8*a* and 8*b* shows the effect of the ADC resolution on the performance of the spike detection unit 16 and template building module 20 respectively, for signals having a high, medium and low SNR. The resolution of the ADC 15 is in the range of 6 to 12 bits. In an embodiment, the resolution of the ADC 15 is 10 bits.

The spike detection unit 16 is configured to detect the one or more action potentials included in the extracellular recording which has been filtered by the signal filtering unit 11 and converted by the ADC 15. The spike detection unit 16 detects the one or more action potentials by comparing an amplitude of the extracellular recording with an amplitude threshold. The amplitude threshold is selected automatically by the spike detection unit 16, although it may also be set manually, as wireless configuration of the spike detection unit 16 as a calibration step based either on trial and error in order to achieve an expected rate of spike detection. Alternatively, a short section of raw data may be transmitted to the remote device 200 for calculation of the amplitude threshold.

In an embodiment, the spike detection unit 16 estimates a standard deviation of a background noise in the extracellular recording. The spike detection unit 16 may select the amplitude threshold based on the estimated standard deviation. The amplitude threshold may be between 3 and 5 times the estimated standard deviation.

The spike detection unit 16 may estimate the standard deviation of the background noise based on the median of the absolute value of the extracellular recording.

In an embodiment, the amplitude threshold, Thr, is automatically set to:

$Thr = 4\sigma_n$ where $$\sigma_n = \text{median}\left(\frac{|x|}{0.6745}\right)$$

and x is the signal.

The spike detection module 10 may include a multiplexer 17 to combine outputs from the spike detection unit 16 for a plurality of extracellular recordings. The combined outputs from the multiplexer 17 are sent to the template building module 20 or the template matching module 30. The output from the spike detection unit 16 consists of a plurality of spike packets which each include a detected action potential. Alternatively, the plurality of spike packets may be output through a serial bus, instead of the multiplexer 17. The spike packets may be transmitted sequentially, with each spike packet being provided with a channel ID and a timestamp.

The template building module 20 comprises a feature extraction unit 21 and a spike classification unit 22. The feature extraction unit 21 is configured to apply a wavelet transform to calculate a plurality of wavelet coefficients for the detected action potential. The wavelet transform is a time-frequency representation of a signal, defined by a convolution between the signal and a set of wavelets. The wavelets are dilated (or contracted) and shifted versions of a unique wavelet function. The wavelet coefficients are obtained by calculating the convolution of the action potential with the wavelet function at different time shifts and (contracted or dilated) scales. The wavelet transform therefore maps a signal which is a function of time only onto a function of the independent dilation and shift variables. Contracted versions of the wavelet function map high-frequency components of the signal, and dilated versions map low-frequency components.

Alternatively, the feature extraction unit 21 may be configured to carry out a principal component analysis to calculate a plurality of principal components for the detected action potential, or may use spike features such as spike amplitude, width, or peak to trough energy.

The feature extraction unit 21 selects a preferred set of wavelet coefficients from the calculated plurality of wavelet coefficients. The preferred set of wavelet coefficients includes one or more coefficients, which indicate a distinction between a plurality of action potentials. The feature extraction unit 21 selects the preferred set of wavelet coefficients based on a calculated deviation from normality. The feature extraction unit 21 may apply a Kolmogorov-Smirnoff test of normality to the calculated wavelet coefficients. The preferred set of wavelet coefficients may include one or more coefficients having the lowest normal distribution. In an embodiment, the preferred set of wavelet coefficients comprises 10 selected wavelet coefficients.

Figure 9:
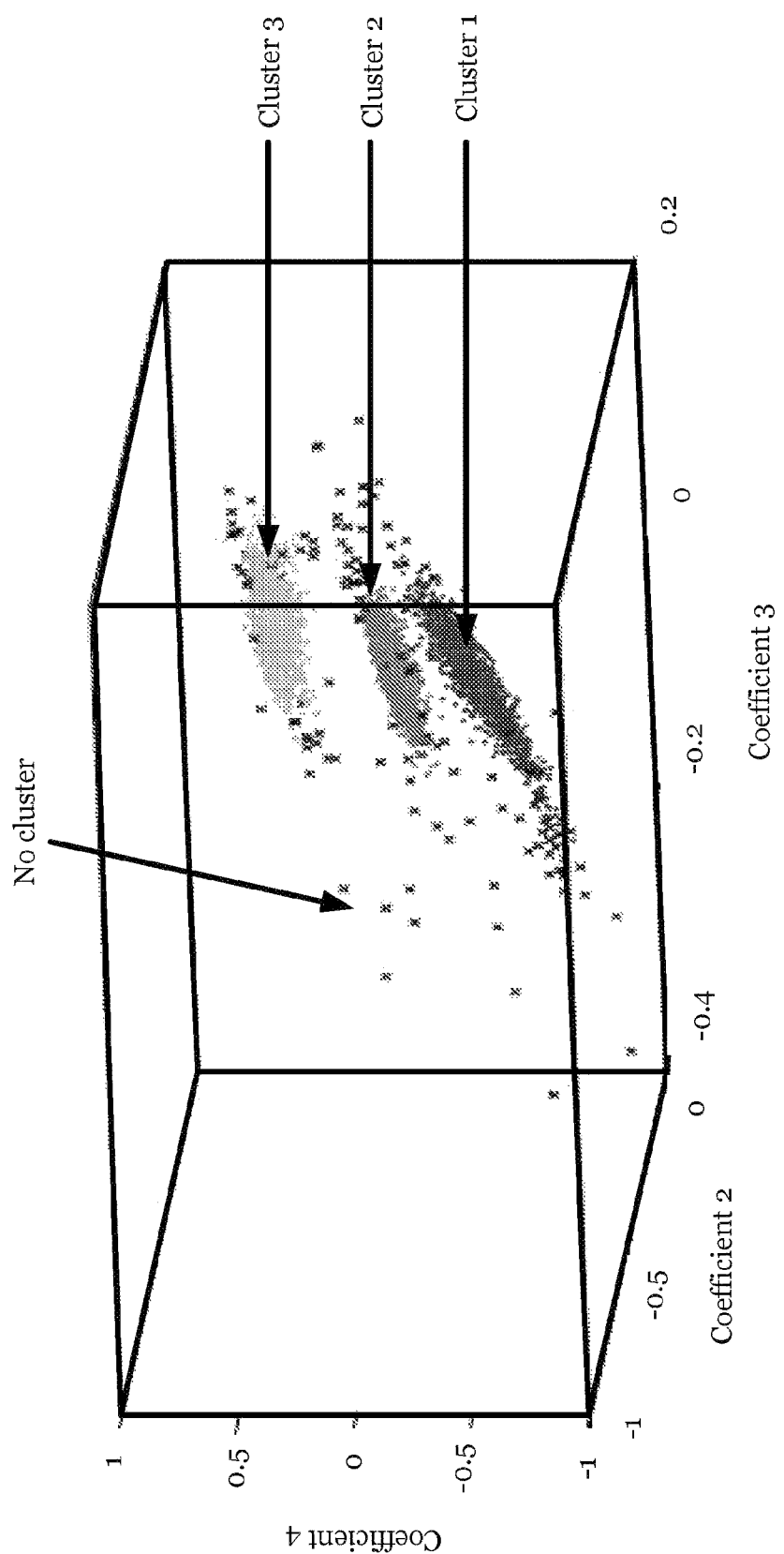
FIG. 9 is a chart showing a distribution of action potentials according to three wavelet coefficients.

FIG. 9 shows a distribution of a plurality of action potentials in a three-dimensional space defined by three preferred wavelet coefficients.

The spike classification unit 22 generates the spike template from one or more principal features shared by a plurality of action potentials in a cluster, the cluster of action potentials having preferred wavelet coefficients which have similar values. The cluster of action potentials may lie in close proximity in a multi-dimensional space defined by the preferred set of wavelet coefficients. The spike classification unit 22 is configured to detect the cluster of action potentials by applying a superparamagnetic clustering (SPC) algorithm. The spike classification unit 22 applies the superparamagnetic clustering algorithm based on the preferred set of wavelet coefficients.

Alternatively, the spike classification unit 22 may be implemented with a K-means classifier, expectation maximization algorithms, a manual delimitation of clusters, or other clustering algorithms.

The SPC algorithm simulates interactions between each data point and its nearest neighbours, wherein a simulated interaction strength falls off exponentially with increasing separation. In a physical analogy with a Potts model, each data point is assigned a random initial state and points in close proximity (i.e. corresponding to a cluster) will change state together. The probability that nearest neighbours will change state together is dependent on a variable which is analogous with temperature in the Potts model.

High temperatures correspond to a low probability of neighbours changing state together. Low temperatures correspond to a high probability of neighbours changing state together, even for a weak interaction strength. There is a "superparamagnetic phase" at a certain medium range of temperature, wherein only those points that are in close proximity will change their state together.

The cluster of action potentials can be detected based on a cluster size criterion. The SPC algorithm calculates a variation in the size of a plurality of clusters as a temperature-analogous variable is changed. In the range analogous to the superparamagnetic phase, an increase in the temperature-analogous variable produces clusters with a relatively large number of members. The temperature-analogous variable may be fixed if the cluster size criterion is met and the one or more principal features may be selected from the one or more detected clusters of action potentials. Alternatively, clusters with a relatively large number of members may be selected from different temperatures.

Figure 10A:
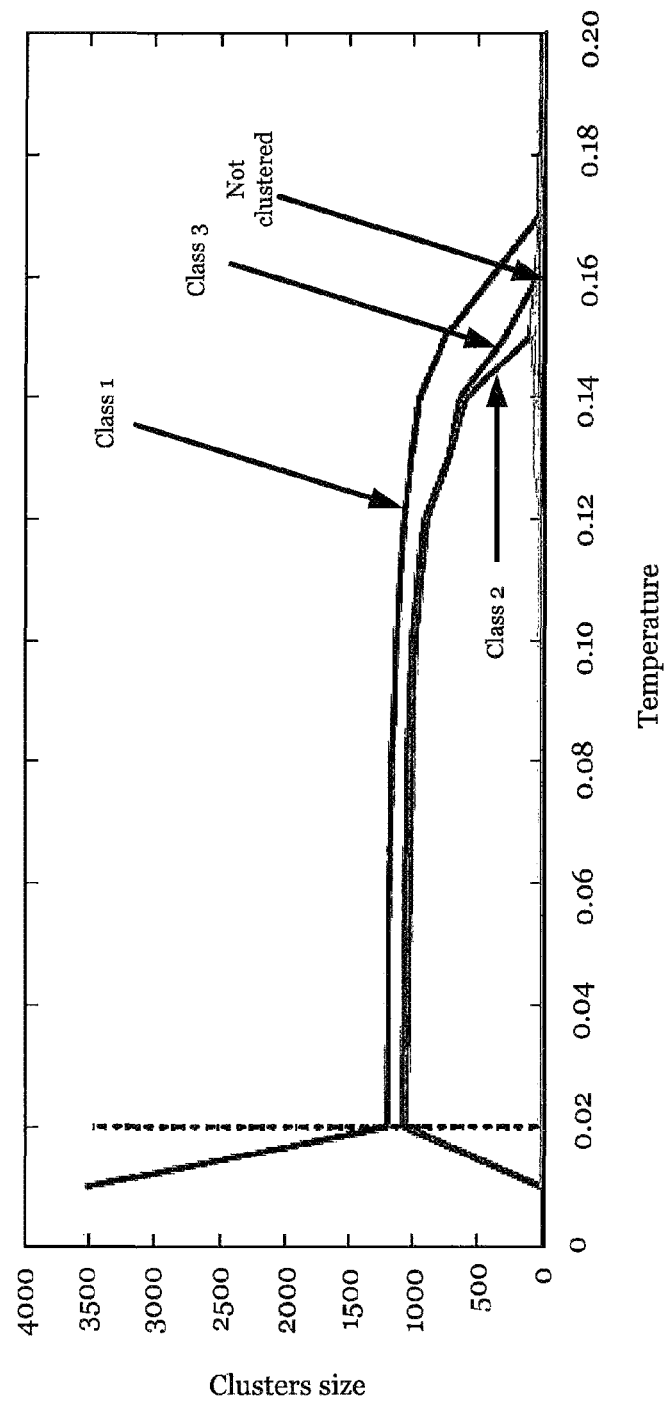
FIG. 10a is a chart showing the effect of a temperature-analogous variable on the size of clusters of action potentials.
Figure 10B:
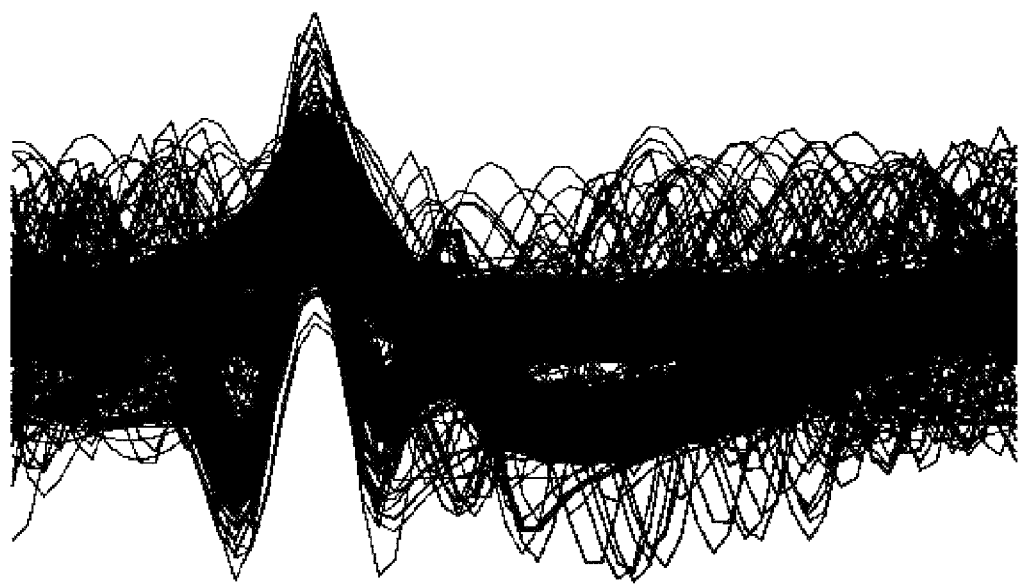
Figure 10C:
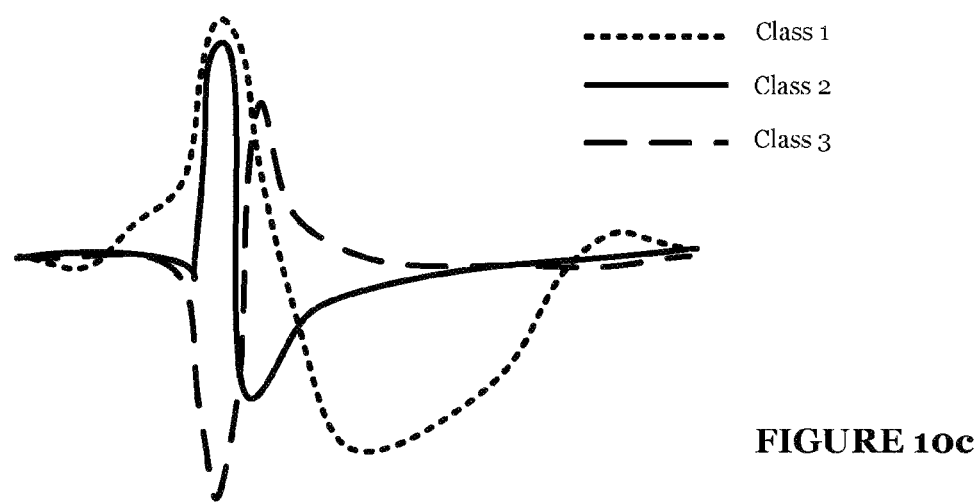

FIG. 10a shows the results of the SPC algorithm applied to the plurality of action potentials in FIG. 9. Cluster size is represented as a function of the temperature-analogous variable, and the vertical dotted line represents a point of transition into the superparamagnetic phase. The one or more principal features used to generate the spike template are selected from the cluster of action potentials meeting the cluster size criterion. FIG. 10b shows a superimposed plurality of action potentials. Heavily clustered areas can be identified, together with peripheral action potentials which are not clustered. FIG. 10c shows the plurality of spike templates generated from the principal features of the clusters of action potentials of FIG. 10c.

The template matching module 30 is arranged to compare the detected action potential with the spike template. The template matching module 30 may receive the output from the multiplexer 17 or the serial bus of the spike detection module 10, including the plurality of spike packets which each include a detected action potential. In some embodiments, the packetized output from the spike detection module 10 may allow the template matching module 30 to operate without an input demultiplexer or an input buffer configured to store a detected action potential for each channel, since use can be made of a channel ID and a timestamp in order for template matches to be performed for spikes on a particular channel.

The template matching module 30 may output a signal to indicate a positive match based on a distance between the detected action potential and the spike template. The template matching module 30 compares the detected action potential with the spike template using a distance metric such as a squared Euclidean distance metric, a Norm 1 distance metric, a Norm infinite distance metric, a Mahalanobis distance metric, a nearest neighbours distance metric or any other suitable distance metric.

FIG. 11 shows the performance and relative processor time required by a template matching module 30 using a variety of suitable distance metrics. In an embodiment, the distance metric may be the Euclidean distance metric, d. The Euclidean distance metric is calculated from the following expression, in which $y_i$ is an element of the detected action potential and $T_i$ is an element of the spike template:

$$d = \sum_{i=1}^{n} (y_i - T_i)^2$$

Alternatively, the template matching module 30 may use the Norm 1 distance metric, which is calculated as:

$$d = \sum_{i=1}^{n} |y_i - T_i|$$

The distance metric used by the template matching module 30 can be selected in order to minimise the level of power consumption, or processor time usage, in the template matching module 30 while maintaining a minimum level of performance.

The template matching module 30 comprises an alignment unit 31 configured to substantially align the detected action potential with the spike template. The alignment unit 31 may align the action potential with the spike template to within a predetermined peak-alignment error, but may also perform alignment on the basis of a signal transition such a leading edge, amplitude threshold.

FIG. 12 shows the effect of the peak-alignment error on the performance of the template matching module 30, for a variety of suitable distance metrics. An incorrect peak-alignment can lead to a reduction in the performance of the template matching module 30 but a reduction in the peak-alignment error leads to an increased level of power consumption in the template matching module 30. The performance of the template matching module 30 should be maintained at 80% or higher. The alignment unit 31 is configured to have a peak-alignment error of less than about 0.125 ms.

The template matching module 30 is configured to select a window size, by cropping the action potential. A reduced window size leads to a reduction in the amount of data stored in the template matching module 30, and a reduction in the complexity of the calculation of a suitable distance metric.

Figure 13:
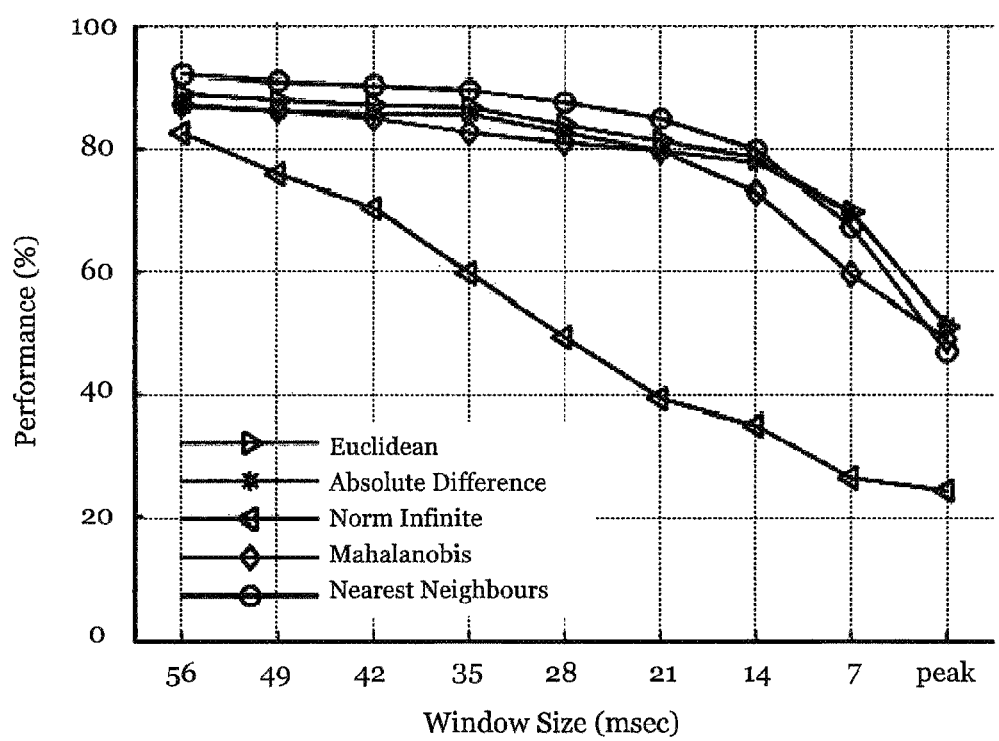
FIG. 13 is a chart showing the effect of window size on template matching performance.

FIG. 13 shows the effect of the window size on the performance of the template matching module 30, for a variety of suitable distance metrics. A reduced window size can lead to a reduction in the performance of the template matching module 30. The performance of the template matching module 30 should be maintained at 70% or higher. The template matching module 30 is configured to use a window size of as low as about 0.5 ms.

The template matching module 30 may be implemented using a processing unit. A processor-based implementation of the template matching module 30 can provide a more efficient operation than using a reconfigurable logic device, such as a field programmable gate array (FPGA).

The invention provides a two-step approach to providing a wireless BCI system. The two-step approach exploits the advantages of both offline and online processing, providing an effective and safe method of neural investigation. The wireless BCI system allows the recognition of specific neurons firing according to the waveform of the neuron and the transmission of neuron activity in a sorted, useable form.

Embodiments of the invention may be used for the control of a prosthetic device. For example, the signals transmitted by the present invention may control one or more prosthetic limbs. A prosthetic limb may be controlled according to the detected activity of one or more neurons responsible for ordinary movement of the missing limb. Other prostheses may be controlled according to the activity of neurons normally responsible for the control of the relevant parts of the body.

Alternatively, embodiments of the invention may be used for the control of electrical stimulation delivered to motor structures including the spinal cord, peripheral nerves or muscles in order to produce movement of the limbs under volitional control of the patient.

Alternatively, embodiments of the invention may be used to monitor the activity of one of more neurons over a period of time. For example, the invention may be used to record neural activity in an animal. The low power wireless BCI of the present invention allows free movement of an animal during recording, providing both a greater variety of experimentation to be performed and an improvement in the welfare of the animal.

Embodiments of the present invention may also be used to monitor neural activity for other clinical applications. In epileptic patients, the present invention may detect the activity of one or more neurons indicating the onset of a seizure. A medical device may be arranged to predict the probably onset of a seizure by monitoring the activity of one or more neurons using the wireless BCI of the present invention, and may be configured to deliver electrical stimulation for prevention of the predicted seizure.

The skilled person will appreciate that a number of modifications may be made to the embodiments described above, which fall within the scope of the present invention, as defined by the claims. Features of various compatible embodiments may be combined. For example, any of the particular filter shapes described is compatible with any of the cut-off frequencies, which are set out above, and the filter combinations are in turn compatible with any of the clustering algorithms described. The skilled person will be able to appreciate, from the teaching described, the extent to which such features can be interchanged while achieving the effects of the present invention.

The invention claimed is:

1. A system for a brain-computer interface, comprising:
a remote device, and
an implantable device comprising:
an integrated circuit comprising:
a signal filtering unit comprising a preamplifier and a filter, and configured to amplify and filter one or more extracellular recordings,
an analogue-digital conversion unit configured to convert the one or more extracellular recordings, and
a spike detection unit configured to detect, within the one or more extracellular recordings, at least one action potential generated by one or more neurons; and
a template matching module arranged to:
compare the at least one detected action potential with one or more predetermined spike templates, and
only in response to a comparison that does not indicate a positive match between the at least one detected action potential and the one or more predetermined spike templates, transmit, to the remote device that is remote from the implantable device, information regarding the at least one detected action potential;
wherein the remote device comprises:
a template building module configured to generate (i) the one or more predetermined spike templates, and (ii) one or more new spike templates based on the information regarding the at least one detected action potential;
wherein the implantable device is configured to receive the one or more new spike templates from the remote device.

2. The system according to claim 1, wherein the template building module is arranged to wirelessly communicate with the implantable device.

3. The system according to claim 1, wherein the signal filtering unit filters the one or more extracellular recordings using one or more of an elliptic filter, a Butterworth filter, a Bessel filter, or a 2nd order filter.

4. The system according to claim 1, wherein a high-pass filter cut-off frequency of the signal filtering unit is about 300 Hz such that a performance value of the spike detection unit is maximized.

5. The system according to claim 1, wherein a low-pass filter cut-off frequency of the signal filtering unit is about 3 kHz such that a performance value of the spike detection unit is maximised.

6. The system according to claim 1, wherein a sampling rate of the analogue-digital conversion unit is reduced to about 7 kHz such that a performance of the spike detection unit remains above 90%.

7. The system according to claim 1, wherein a resolution of the analogue-digital conversion unit is 6 bits or 10 bits such that a performance of the spike detection unit remains above 90%.

8. The system according to claim 1, wherein a resolution of the analogue-digital conversion unit is 6 bits or 10 bits such that a performance of the template building module remains above 50%.

9. The system according to claim 1, wherein the spike detection unit is configured to automatically select an amplitude threshold based on an estimate of a standard deviation of a background noise in the one or more extracellular recordings.

10. The system according to claim 9, wherein the standard deviation of the background noise is estimated based on a median of an absolute value of the filtered one or more extracellular recordings.

11. The system according to claim 1, wherein the template building module comprises:
a feature extraction unit configured to calculate a set of features for each of the at least one detected action potential; and
a spike classification unit configured to generate the one or more predetermined spike templates from one or more principal features shared by a cluster of action potentials having similar features.

12. The system according to claim 11, wherein the feature extraction unit is configured to at least one of: extract one or more data points for each detected action potential, calculate a plurality of principal components, or calculate a wavelet transform comprising a plurality of wavelet coefficients and select a preferred set from the plurality of wavelet coefficients based on a calculated deviation from normality according to a Kolmogorov-Smirnoff test.

13. The system according to claim 12, wherein the spike classification unit is configured to at least one of: detect the cluster of action potentials by applying a superparamagnetic clustering algorithm based on at least one of: the preferred set of wavelet coefficients, the plurality of principal components, or the extracted one or more data points, or detect the cluster of action potentials used to generate the one or more predetermined spike templates based on a cluster size criterion.

14. The system according to claim 1, wherein the template matching module compares the at least one detected action potential with the one or more predetermined spike templates using one of a squared Euclidean distance metric, a Norm 1 distance metric, a Norm infinite distance metric, a Mahalanobis distance metric, and a nearest neighbours distance metric.

15. The system according to claim 1, wherein the template matching module comprises a peak alignment unit configured to substantially align the at least one detected action potential with the one or more predetermined spike templates, to within a predetermined peak-alignment error.

16. The system according to claim 1, wherein the template matching module is configured to use a window size of about 0.5 ms.

17. The system according to claim 1, further comprising a selector configured to enable a user to manually select an amplitude threshold for the spike detection unit.

* * * * *